United States Patent
Eggen et al.

(10) Patent No.: US 9,943,682 B2
(45) Date of Patent: Apr. 17, 2018

(54) METHOD AND APPARATUS FOR DETERMINING SUITABILITY OF A LEAD IMPLANT LOCATION

(71) Applicant: Medtronic, Inc., Minneapolis, MN (US)

(72) Inventors: Michael D Eggen, Chisago City, MN (US); Tarek D Haddad, Minneapolis, MN (US); Paul A Iaizzo, White Bear Lake, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 224 days.

(21) Appl. No.: 14/696,242

(22) Filed: Apr. 24, 2015

(65) Prior Publication Data

US 2015/0320996 A1    Nov. 12, 2015

Related U.S. Application Data

(60) Provisional application No. 61/989,226, filed on May 6, 2014.

(51) Int. Cl.
*A61N 1/05* (2006.01)
*A61N 1/08* (2006.01)

(52) U.S. Cl.
CPC ........... *A61N 1/056* (2013.01); *A61N 1/0573* (2013.01); *A61N 1/08* (2013.01); *A61N 2001/083* (2013.01)

(58) Field of Classification Search
CPC ................................ A61N 1/0573; A61N 1/08
See application file for complete search history.

(56) References Cited

U.S. PATENT DOCUMENTS

| | | | |
|---|---|---|---|
| 5,335,668 A | 8/1994 | Nardella | |
| 5,792,204 A | 8/1998 | Snell | |
| 6,714,086 B1 | 3/2004 | Landrith | |
| 6,714,806 B2 | 3/2004 | Iaizzo et al. | |
| 7,158,838 B2 * | 1/2007 | Seifert ............. | A61M 25/0097 604/528 |
| 7,991,484 B1 | 8/2011 | Sengupta et al. | |
| 8,180,454 B2 | 5/2012 | Greenberg et al. | |
| 8,326,418 B2 | 12/2012 | Sommer et al. | |
| 8,355,774 B2 | 1/2013 | Markowitz et al. | |
| 8,649,851 B2 | 2/2014 | Cholette | |
| 2003/0199938 A1 | 10/2003 | Smits et al. | |
| 2014/0018873 A1 | 1/2014 | Gunderson | |

OTHER PUBLICATIONS

Boosted Models: A guide to the gbm package, by Greg Ridgeway, May 23, 2012.

(Continued)

*Primary Examiner* — Amanda Patton

(57) ABSTRACT

Method and systems of determining adequacy of fixation of a medical lead type having a fixation helix are disclosed. The lead of the medical lead type is placed at a desired location within a patient's body and the fixation helix is screwed into tissue at that location. One or more parameters, associated with the lead, are measured at the location. Based upon the measured one or more parameters, determining a number of turns that the helix is embedded into the tissue at the location.

10 Claims, 4 Drawing Sheets

(56) References Cited

OTHER PUBLICATIONS

Saxonhouse et al "Current of Injury Predicts Adequate Active Lead Fixation in Permanent Pacemaker/Defibrillation Leads". Journal of the American College of Cardiology vol. 45, No. 3, 2005.
Roelke M1, Bernstein AD, Parsonnet V. Serial lead impedance measurements confirm fixation of helical screw electrodes during pacemaker implantation. Pacing Clin Electrophysiol. Apr. 2000;23 (4 Pt 1):488-92.

\* cited by examiner

METHOD AND APPARATUS FOR DETERMINING SUITABILITY OF A LEAD IMPLANT LOCATION

CROSS-REFERENCE TO RELATED APPLICATIONS

This application claims the benefit of U.S. Provisional Application No. 61/989,226, filed on May 6, 2014. The disclosure of the above application is incorporated herein by reference in its entirety.

TECHNICAL FIELD

This disclosure relates to implantable medical devices and, more particularly, to implantation of cardiac leads.

BACKGROUND

For some types of cardiac pacing leads, it can be difficult to determine how well the fixation mechanism or pacing electrode is contacting tissue. For example, for a lead having a fixed or extendable helix, there may be no easy to interpret indicator visible in fluoroscopy that the helix has turned and penetrated the tissue. While the fact that the helix is fully extended may be determinable, the number of turns of the helix that have entered the heart's tissue may be unknown.

With new therapies such as LV endocardial pacing, lead revisions become more difficult and lead fixation becomes increasingly important. During implant of these types of leads, it would be especially desirable to precisely determine when the helix is fully fixed in the myocardium using available pacing-related parameters.

To address this issue, a number of systems have been proposed and/or developed. For example, monitoring of impedance levels associated with the helix and/or other electrodes as the helix is screwed into tissue is disclosed in, U.S. Pat. No. 6,714,086 issued to Iaizzo et al. and incorporated herein by reference in its entirety. An alternative approach is based upon measurement of current of injury (COI) as disclosed in U.S. Pat. No. 6,714,086 issued to Cholette, also incorporated herein by reference in its entirety.

SUMMARY

The inventors have determined that, in the case of leads employing helical fixation mechanisms which also serve as electrodes, a number of measurable parameters vary as the helix is screwed into heart tissue. These include r-wave amplitude, current of injury, pacing threshold and pacing impedance. However, the inventors have also determined that the values of these parameters individually are inadequate to accurately characterize the fixation state. In particular, the values of the parameters vary substantially from patient to patient, so that merely setting a target threshold or a range for parameter as indicative of adequate fixation is not sufficient.

To address this issue, rather than merely attempting to correlate measured parameters with a general characterization of fixation quality, the inventors have analyzed these parameters in more detail as a function of the number of turns of a fixation helix that have actually entered heart tissue. For purposes of this research, Medtronic SelectSecure 3830 leads were implanted in the left ventricle of isolated, beating swine hearts via a transseptal approach using direct visualization. Current of injury (COI), pacing impedance (PZ), stimulation threshold (pacing capture threshold—PCT), slew rate, signal amplitude (R-wave amplitude), and signal duration (EGM R-wave duration) were measured using a Medtronic 2290 PSA for the following helix conditions: touching, 1 turn fixed, 2 turns fixed, and overtorqued (>2 turns). In a separate set of hearts (N=3) the force required to dislodge the lead using the same conditions was measured with a uniaxial extension tester.

The results of this testing were that the COI, PCT, PZ, R-wave, and EGM R-wave duration all significantly increased with an increasing number helix turns ($p<0.001$). The slew rate did change significantly with fixation. COI could be used to differentiate between touching and 1 turn fixed (1.11+/−1.28 vs. 3.86+/−3.55 mV, $p<0.04$), and between 1 turn fixed and 2 turns fixed (3.86+/−3.55 vs. 9.41+/−5.87 mV, $p<0.001$). The force required to dislodge the lead did not trend significantly with the number of turns.

Based upon these results, the inventors have determined that pacing threshold, current of injury (COI max/and/or COI/80), impedance and R-wave amplitude were the most useful in determining the number of turns the helix had penetrated into heart tissue.

However, the values of these parameters varied widely between patients, such that for each parameter in each helix condition (touching, 1 turn fixed, 2 turns fixed, and overtorqued >2 turns) the range of each of the measured parameters substantially overlapped the range for adjacent helix conditions.

Results of such testing are set forth below in table 1.

TABLE 1

| Parameter | Electrical Results | | | | |
| --- | --- | --- | --- | --- | --- |
| | Touching | 1 Turn Fixed | 2 Turns Fixed | Overtorqued | P-value (trend) |
| COI (mV)*† | 1.12 ± 1.28 | 3.86 ± 3.55 | 9.41 ± 5.87 | 10.14 ± 5.59 | <0.001 |
| PCT (V@ 0.4 ms)‡ | 1.00 ± 0.38 | 1.24 ± 0.45 | 1.55 ± 0.59 | 2.91 ± 1.23 | <0.001 |
| PZ (ohms)† | 506 ± 179 | 577 ± 213 | 779 ± 262 | 878 ± 333 | <0.001 |
| R-wave (mV) | 5.24 ± 2.93 | 5.95 ± 2.86 | 10.03 ± 5.77 | 10.48 ± 5.30 | <0.001 |
| Slew Rate (V/s) | 1.27 ± 1.01 | 1.27 ± 0.90 | 1.28 ± 0.79 | 1.23 ± 0.52 | 0.38 |
| EGM Duration (ms)† | 139 ± 41 | 174 ± 53 | 200 ± 34 | 221 ± 30 | <0.001 |

\*p < 0.05 1 turn fixed vs. touching
†p < 0.05 2 turns fixed vs. 1 turn fixed
‡p < 0.05 Overtorqued vs. 2 turns fixed Because of the high degree of overlap, a simple comparison of a single parameter to a threshold or range to determine the number of turns is insufficient. In order to overcome this problem, the inventors have developed multivariable analytic techniques as described below to overcome this difficulty. The inventors have also devised an implantation techniques to determine a suitable location for a pacing lead, incorporating the analysis techniques.

In one embodiment of the invention, a combinatorial analysis of the individually measured parameters is employed to determine the number of turns of the helix that have entered the heart tissue. The determined number of turns is displayed to the implanting physician. If the displayed number is less than the desired number (e.g. 2), the physician repositions the lead by further rotating the helix. Responsive to the desired number of turns being reached, the physician then determines whether one or more pacing related characteristics (e.g. R-wave amplitude, pacing threshold) are acceptable. If the measured parameter or parameters is/are acceptable, the lead may stay where it is. Otherwise, the lead is repositioned by moving it to an alternate location.

In a second a derived multivariate transfer function relating the measured parameters as a group to the number of turns is employed. The determined number of turns is displayed to the implanting physician. If the displayed number is less than the desired number (e.g. 2), the physician repositions the lead by further rotating the helix. Responsive to the desired number of turns being reached, the physician then determines whether one or more pacing related characteristics (e.g. R-wave amplitude, pacing threshold) are acceptable. If the measured parameter or parameters is/are acceptable, the lead may stay where it is. Otherwise, the lead is repositioned by moving it to an alternate location.

In some embodiments, parameters measured and analyzed to determine the number of turns of the helix that have entered the heart tissue include all four of pacing threshold, current of injury (COI max/and/or COI/80), impedance and R-wave amplitude. In some embodiments, a lesser plurality of these parameters, for example COI, Impedance and threshold may be employed. In some embodiments, only two of these measurements may be employed.

The details of one or more aspects of the disclosure are set forth in the accompanying drawings and the description below. Other features, objects, and advantages of the disclosure will be apparent from the description and drawings, and from the claims.

DETAILED DESCRIPTION

Figure 1:
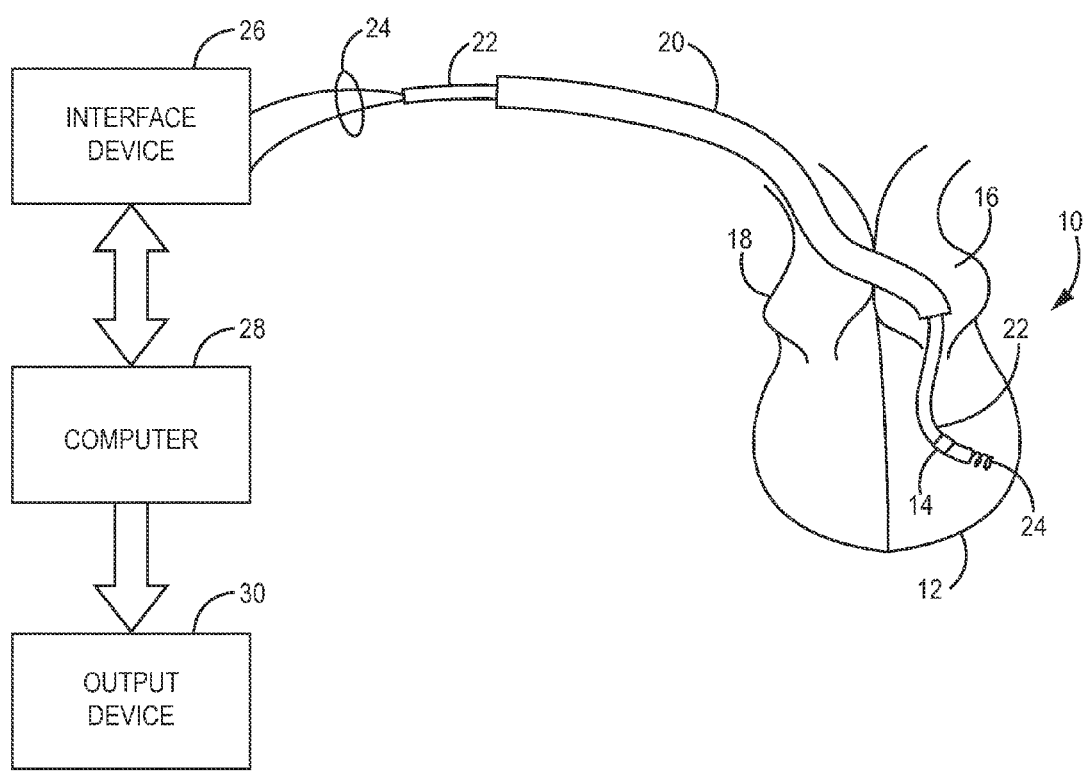
FIG. 1 is a diagram illustrating a lead in the process of implantation and an associated device system for obtaining the parameters to be measured and for providing an indication of the number if turns of the helix that have entered heart tissue.

FIG. 1 illustrates a patient's heart 10, with a lead 22, introduced into the left ventricle 12 by means of an introducer catheter 20. The lead is introduced into the left ventricle by means of an atrial trans-septal puncture allowing the introducer catheter to enter the left atrium 16 and to direct the lead into the left ventricle 12. A ventricular trans-septal puncture may also be employed. The helical electrode 24 is shown extending for two turns from the lead and adjacent the wall of the left ventricle 12.

In other embodiments, the lead may be placed in other locations, including the atria and the right ventricle. The number of turns of the helix may vary as well. The specific relationships between the measured parameters and the number of turns may vary with lead configuration and location. Correspondingly, the number of turns indicative of proper fixation may also vary.

The lead is coupled by conductors 24 to an interface device 26 such as a Medtronic Model 2290 PSA (Pacing Systems Analyzer). The interface device 26 is used to make the measurements of the parameters and provides the measurements to the computer 28. In some embodiments, the collection of the measured parameters may be done under physician control. In other embodiments, collection of the parameters may be done under control of computer 28 or under control of software resident in the interface device 26. The computer 28 employs the analytical methodology of the present invention to derive a turn number and provide it to the output device, which may be a conventional display. The analytical techniques of the present invention, as discussed below, may be embodied in stored software as executed by computer 28.

Figure 2:
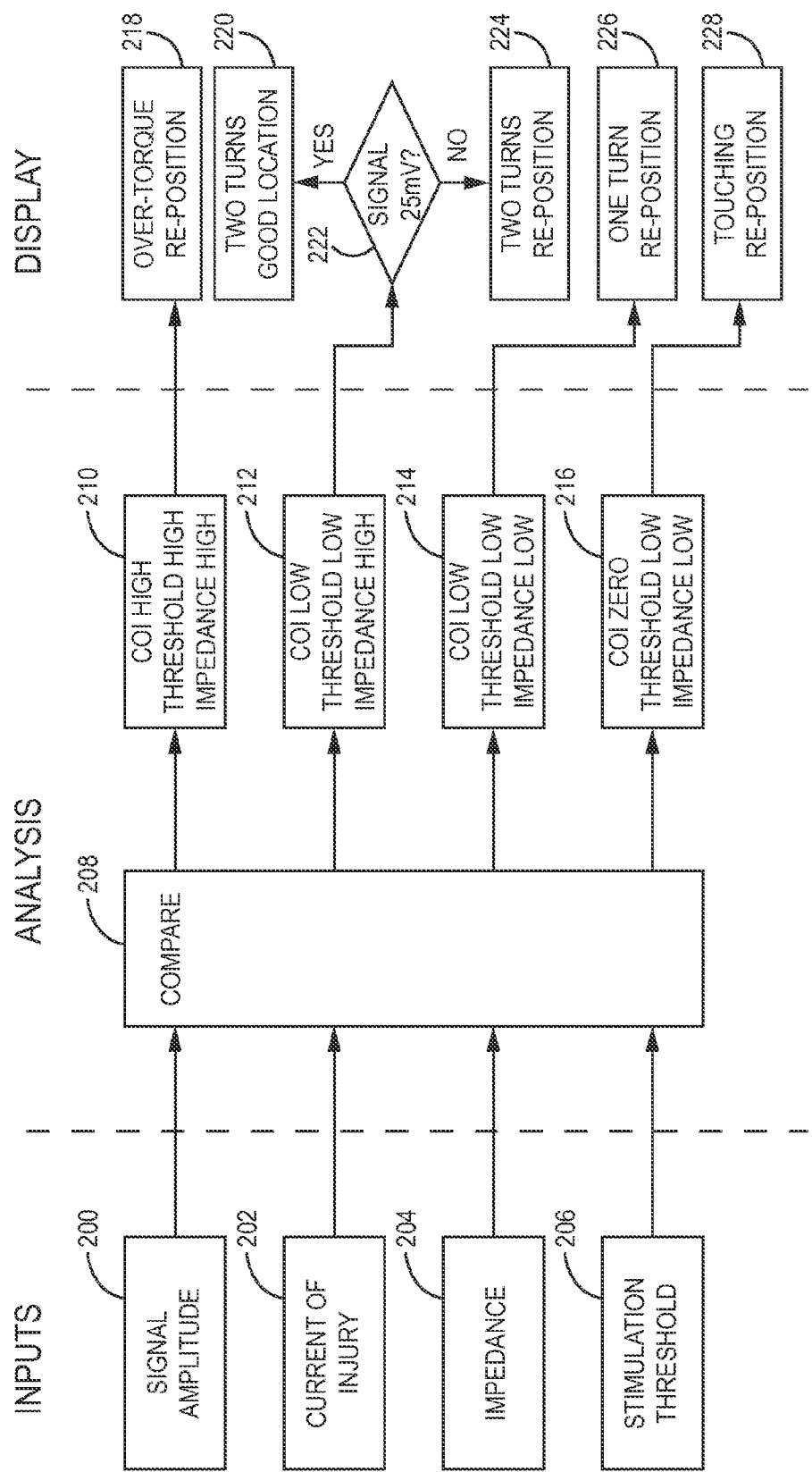
FIG. 2 is a flow chart illustrating a first embodiment of the analytical method performed by the device system of FIG. 1.

FIG. 2 is a flow chart illustrating operation of a first embodiment of an analysis technique according to the present invention. At 200, 202, 204, 206, the computer 28 (FIG. 1) receives the input measured parameters from the interface device 26. In this case, the input measured parameters include all four of pacing threshold, current of injury (COI max/and/or COI/80), impedance and R-wave amplitude. In other embodiments a lesser plurality of these parameters may be employed. In order to determine the number of turns of the helix that have entered heart tissue, three of the parameters, pacing threshold, current of injury (COI max/and/or COI/80) are compared by the computer 28 to pre-set ranges and/or thresholds as illustrated at 210, 212, 214 and 216. The outcomes of the comparisons are used to determine the number of turns. Exemplary comparison values are set forth below.

For purposes of block 210, COI may be considered high if it exceeds 25 mV. Pacing threshold may be considered high if it exceeds 2.5V at a 4 ms. pulse width. Pacing impedance may be considered high if it exceeds 3000 ohms. If all three parameters are considered high, the likely cause is over-torquing of the lead. At 218, the computer then causes display 30 to indicate that the lead is over-torqued and suggest re-positioning of the lead. After re-positioning of the lead, the parameters are measured again and the analytical process begins anew.

For purposes of block 212, COI may be considered high if it is between 10 and 25 mV. Pacing threshold may be considered low if it is between 0.5 and 2.5V at a 4 ms. pulse width. Pacing impedance may be considered high if it is between 800 and 1500 ohms. If all three parameters fall in these ranges, the likely cause is that the lead is properly affixed with two turns of the helix embedded in the tissue. The computer checks at 222 to determine whether the R-wave is adequate to allow reliable sensing. In this case, an amplitude of 5 mV or greater is considered adequate. If the sensing amplitude is adequate, at 220, the computer then causes display 30 to indicate that the lead is adequately affixed and that the implantation site is acceptable. If the sensing amplitude is inadequate, at 224 the computer then causes display 30 to indicate that the lead is adequately affixed but that the implantation site is not acceptable and suggests re-positioning of the lead. After re-positioning of the lead, the parameters are measured again and the analytical process begins anew.

For purposes of block 214, COI may be considered low if it is greater than zero but less than 3 mV. Pacing threshold may be considered low if it is less than 0.5V at a 4 ms. pulse width. Pacing impedance may be considered low if it is less than 500 ohms. If all three parameters meet these criteria, the likely cause is that the lead is not fully affixed and has only about one turn of the helix embedded in heart tissue. At 226, the computer then causes display 30 to indicate that only one turn of the helix is embedded and to suggest re-positioning of the lead by additionally rotating the helix into tissue. After re-positioning of the lead, the parameters are measured again and the analytical process begins anew.

For purposes of block 216, COI may be considered to be zero if it is insignificantly different from zero. Pacing threshold may be considered low if it is less than 0.5V at a 4 ms. pulse width. Pacing impedance may be considered low if it is less than 500 ohms. If all three parameters meet these criteria, the likely cause is that the lead is not fully affixed and the helix is only touching heart tissue. At 228, the computer then causes display 30 to indicate that the helix is only touching heart tissue and to suggest re-positioning of the lead by additionally rotating the helix into tissue. After re-positioning of the lead, the parameters are measured again and the analytical process begins anew.

Figure 3:
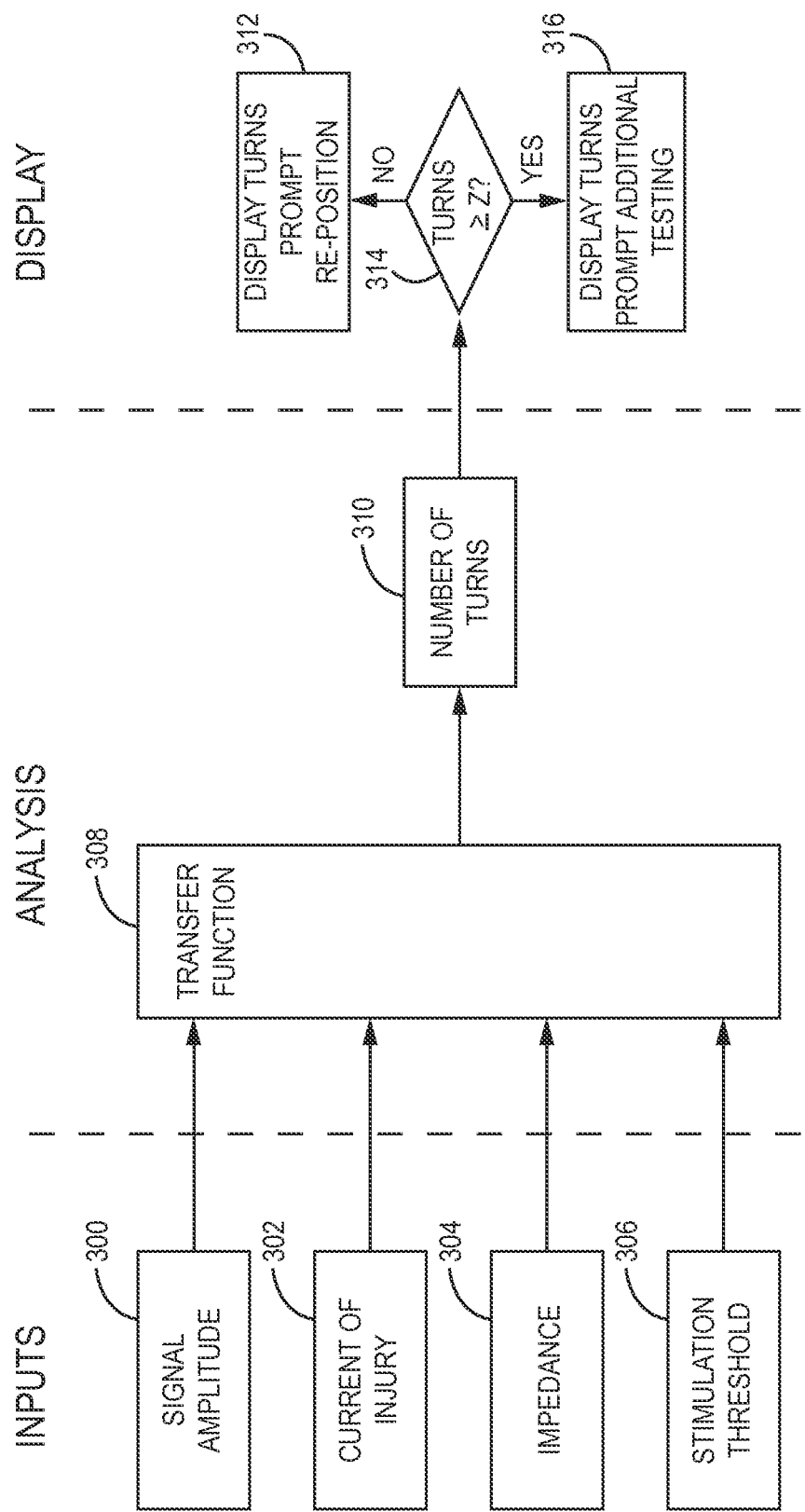
FIG. 3 is a flow chart illustrating a second embodiment of the analytical method performed by the device system of FIG. 1.

FIG. 3 is a flow chart illustrating operation of a second embodiment of an analysis technique according to the present invention. At 300, 302, 304, 306, the computer 28 (FIG. 1) receives the input measured parameters from the interface device 26. In this case, the input measured parameters include all four of pacing threshold, current of injury (COI max/and/or COI/80), impedance and R-wave amplitude. In order to determine the number of turns of the helix that have entered heart tissue, all for of these parameters are employed. In other embodiments a lesser plurality of these parameters may be employed. At 308 the computer applies a derived transfer function relating the input parameters to the number of turns of the helix that are embedded in heart tissue.

One method of deriving an appropriate transfer function is by means of a Gradient Boosted Model, for example by means of the "gbm package" available as described in the article entitled "Generalized Boosted Models: A guide to the gbm package", by Greg Ridgeway, May 23, 2012, incorporated herein by reference in its entirety.

By means of application of this software package to the test results as discussed above, the inventors were able to produce an appropriate transfer function. Because of the complexity if the relationships between the measured parameters and the resultant number of turns, the transfer function itself is embodied as a look-up table stored within the computer's memory.

It is expected that other lead configurations and/or other lead implantation locations (e.g. the right ventricle or the atria) will require their own transfer functions, based upon test results taken using the particular lead under consideration and the chamber in which it is to be implanted. Additionally, it is understood that appropriate transfer functions may be derived using other statistical software packages and/or other statistical approaches.

At 30, the computer provides the number of turns based upon the input parameters. If the number of turns is less than two at 314, at 312 the computer causes the display to display the number of turns (e.g. touching the heart wall or only one turn embedded), to indicate that the lead is not yet properly affixed and to suggest repositioning the lead by turning the helix further into the heart tissue. After repositioning of the lead, the parameters are measured again and the analytical process begins anew If the number of turns is at least two at 314, at 316 the computer causes the display to display the number of turns (e.g. two or in some embodiments "over-torqued"), to indicate that the lead is fully affixed and to testing the lead to determine whether pacing parameters such as pacing threshold and/or sense amplitude are acceptable. If the pacing parameters are acceptable the lead may stay where it is. If the pacing parameters are not acceptable the lead may be repositioned. At the physician's discretion, the lead may be repositioned if the computer indicates that the lead has been over-torqued. After re-positioning of the lead, the parameters are measured again and the analytical process begins anew.

Figure 4:
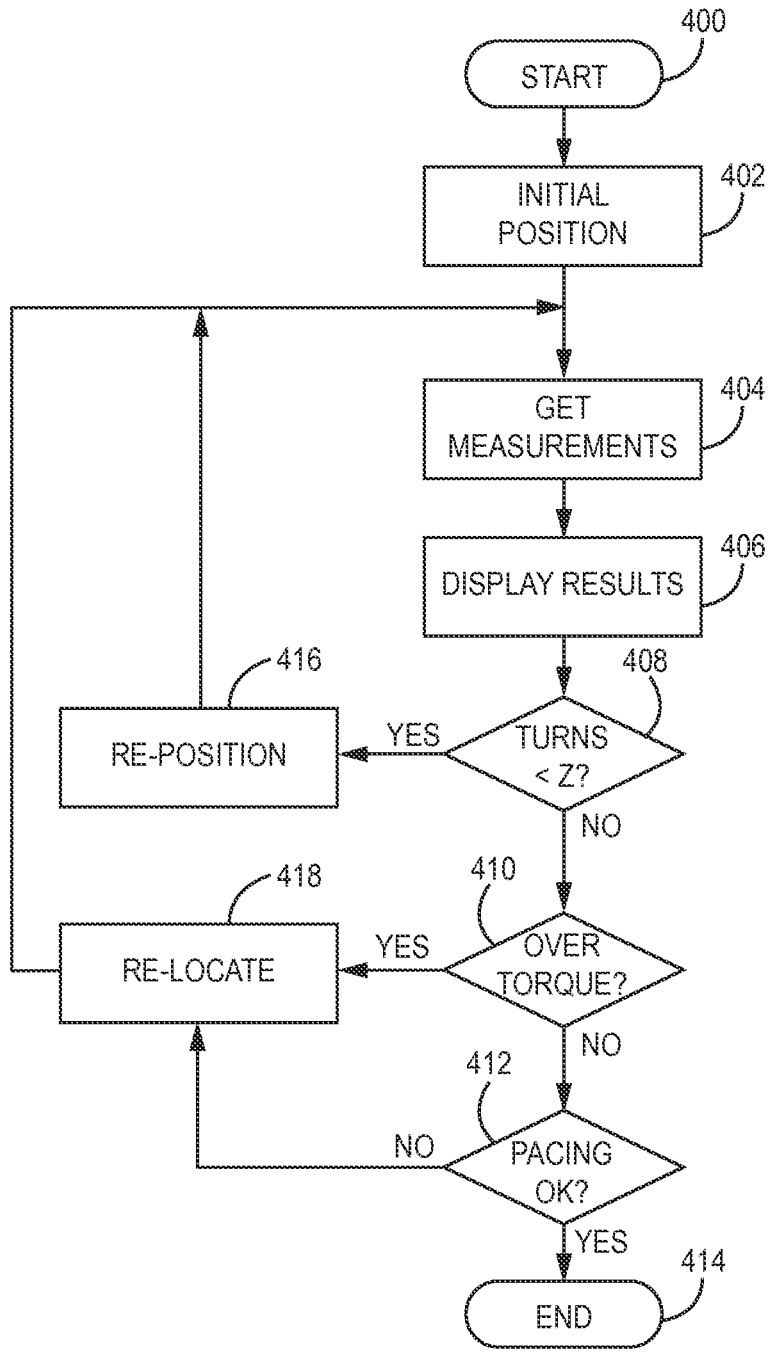
FIG. 4 is a flow chart illustrating a method of implant employing an analytical method according to the invention.

FIG. 4 is a flow chart illustrating a method of implanting a lead according to the invention. At 400, the implant process is begun by advancing the lead into the heart. The physician initially positions the lead at a desired location at 402 and rotates the helix in an attempt to embed it into the heart tissue. The physician then applies the analytical technique of the invention, for example by use of the system illustrated in FIG. 1 to make measurements of the relevant parameters at 404 and displaying the derived number of turns at 406. If the number of turns is less than two at 408, the physician may reposition the lead at 416 by rotating the helix to advance it further into heart tissue. The analytical process is then repeated as discussed above.

If the number of turns is at least two and the system indicates an over-torque condition at 410, the physician may relocate the lead at 418. Otherwise, the physician may conduct additional testing at 412 to determine whether the location is otherwise suitable for cardiac pacing and sensing as discussed above. Alternatively, such additional tests may be incorporated into the analytical method performed by the system as described in conjunction with step 222, FIG. 2.

If the location is suitable for cardiac pacing and sensing, the physician may leave the lead in place. Otherwise, the physician may re-position the lead at another location at 418, and the analytical process is re-started at 404 as described above.

While the above description is based upon the use of a conventional stand-alone computer and an associated interface device, it is also of course possible to practice the invention by combining the functionality of both devices into a single device. In either case, it is believed that the most likely mechanism for practicing the analytical process disclosed above will be by means of a microprocessor executing an instruction set stored in a non-transitory storage medium and corresponding to the flow charts of FIG. 2 or 3. However, in the case of the analytical technique of FIG. 2, it is possible that the analytical technique could be performed by the implanting physician as part of the implantation process. In such case, the physician would compare the parameters measured by the interface device 26 to defined ranges and thresholds to determine the number of turns that the helix that are embedded in heart tissue.

The specific lead discussed above is what is commonly referred to as a screw-in endocardial pacing lead. Its helix extends for two turns from the end of the lead body, as described above. Other such leads may have more or less turns extending from the lead. In such cases, correspondingly, a greater or lesser number of turns may have to be embedded to define a fully fixated condition. Other screw-in leads are also known for use as myocardial pacing leads, screwed into the outer surface of the heart wall. The invention is believed applicable to such leads as well.

It should also be noted that screw-in leads may also be employed for stimulation of other tissue types besides cardiac tissue. The present invention is believed to be adaptable to such uses as well. In such cases, thresholds for stimulation for the tissue type and amplitudes of signals sensed from the tissue would be substituted for pacing threshold and R-wave amplitude as is appropriate. Additionally, other measured parameters of the other tissue types may be substituted for those discussed above or may be used in addition to those discussed above.

In conjunction with the above disclosure, we claim:

1. A method of determining adequacy of fixation of a medical lead type having a fixation helix, comprising:
    placing the lead of the type at a desired location within a patient's body and screwing the fixation helix into tissue at that location;
    measuring one or more parameters associated with the lead at the location; and
    based upon the measured one or more parameters, determining a number of turns that the helix is embedded into the tissue at the location;
    wherein the measured parameters include a plurality of: stimulation threshold, signal amplitude, current of injury and impedance.

2. A method according to claim 1 wherein the determining step comprises comparing the measured parameters to defined ranges or thresholds and based upon the results of the comparisons in combination with one another, determining the number of turns.

3. A method according to claim 1 wherein the determining step comprises application of a transfer function derived from testing of leads of the type.

4. A method according to claim 1 wherein the tissue is heart tissue.

5. A method of implanting a medical lead type having a fixation helix, comprising:
    placing the lead of the type at a desired location within a patient's body and screwing the fixation helix into tissue at that location;
    measuring one or more parameters associated with the lead at the location;
    based upon the measured one or more parameters, determining a number of turns that the helix is embedded into the tissue at the location;
    based upon the number of turns, determining whether the lead is properly placed; and
    if the lead is not properly placed, repositioning the lead;
    wherein the measured parameters include a plurality of: stimulation threshold, signal amplitude, current of injury and impedance.

6. A method according to claim 5 wherein the determining step comprises comparing the measured parameters to defined ranges or thresholds and based upon the results of the comparisons in combination with one another, determining the number of turns.

7. A method according to claim 5 wherein the determining step comprises application of a transfer function derived from testing of leads of the type.

8. A method according to claim 5 wherein repositioning the lead comprises rotating the fixation helix to screw it further into the tissue.

9. A method according to claim 5 wherein repositioning the lead comprises moving the lead to a new location.

10. A method according to claim 5 wherein the tissue is heart tissue.

* * * * *